(12) United States Patent
McKenzie (10) Patent No.: US 9,439,878 B2
(45) Date of Patent: Sep. 13, 2016

(54) USE OF LUMEFANTRINE AND RELATED COMPOUNDS IN THE TREATMENT OF CANCER

(76) Inventor: Douglas Tyler McKenzie, San Diego, CA (US)

( * ) Notice: Subject to any disclaimer, the term of this patent is extended or adjusted under 35 U.S.C. 154(b) by 311 days.

(21) Appl. No.: 13/134,212

(22) Filed: Jun. 1, 2011

(65) Prior Publication Data

US 2011/0300137 A1    Dec. 8, 2011

Related U.S. Application Data

(60) Provisional application No. 61/396,797, filed on Jun. 3, 2010.

(51) Int. Cl.

| | | |
|---|---|---|
| *A61K 31/137* | (2006.01) | |
| *A61K 31/155* | (2006.01) | |
| *A61K 31/165* | (2006.01) | |
| *A61K 31/19* | (2006.01) | |
| *A61K 31/337* | (2006.01) | |
| *A61K 31/357* | (2006.01) | |
| *A61K 31/427* | (2006.01) | |
| *A61K 31/44* | (2006.01) | |
| *A61K 31/47* | (2006.01) | |
| *A61K 31/472* | (2006.01) | |
| *A61K 31/4725* | (2006.01) | |
| *A61K 31/4965* | (2006.01) | |
| *A61K 31/5025* | (2006.01) | |
| *A61K 31/506* | (2006.01) | |
| *A61K 31/513* | (2006.01) | |
| *A61K 31/517* | (2006.01) | |
| *A61K 31/5377* | (2006.01) | |
| *A61K 31/635* | (2006.01) | |
| *A61K 31/69* | (2006.01) | |
| *A61K 38/07* | (2006.01) | |

(52) U.S. Cl.
CPC ............ *A61K 31/137* (2013.01); *A61K 31/155* (2013.01); *A61K 31/165* (2013.01); *A61K 31/19* (2013.01); *A61K 31/337* (2013.01); *A61K 31/357* (2013.01); *A61K 31/427* (2013.01); *A61K 31/44* (2013.01); *A61K 31/47* (2013.01); *A61K 31/472* (2013.01); *A61K 31/4725* (2013.01); *A61K 31/4965* (2013.01); *A61K 31/506* (2013.01); *A61K 31/5025* (2013.01); *A61K 31/513* (2013.01); *A61K 31/517* (2013.01); *A61K 31/5377* (2013.01); *A61K 31/635* (2013.01); *A61K 31/69* (2013.01); *A61K 38/07* (2013.01)

(58) Field of Classification Search
CPC .................................................. A61K 31/137
See application file for complete search history.

(56) References Cited

PUBLICATIONS

FDA Approved Label for Coartem (artemether/lumefantrine) tablets revised Apr. 2009. Accessed from http://www.accessdata.fda.gov on Jan. 2, 2013.*
Sausville et al. Cancer Research, 2006, vol. 66, pp. 3351-3354.*
Johnson et al. British J. of Cancer, 2001, 84(10):1424-1431.*

* cited by examiner

*Primary Examiner* — James D Anderson

(57) ABSTRACT

The present application discloses the use of the anti-malarial drug lumefantrine and related compounds in the treatment of cancer.

7 Claims, 7 Drawing Sheets

USE OF LUMEFANTRINE AND RELATED COMPOUNDS IN THE TREATMENT OF CANCER

CROSS-REFERENCE TO RELATED APPLICATIONS

The present application claims benefit of provisional application U.S. 61/396,797, filed on Jun. 3, 2010, which is hereby incorporated by reference in its entirety.

FIELD OF INVENTION

The present disclosure concerns methods for treating cancer.

BACKGROUND

The human body has evolved complex mechanisms to perpetuate and protect itself. Sometimes, however, those mechanisms go awry, and either exacerbate or, indeed, cause serious pathologies such as cancer. Despite intensive work and numerous therapeutic advances, a need remains for broadly applicable cancer treatments, especially for tumors that are refractory to current treatments, or become resistant in the course of therapy. Consequently, a continuing need exists for cancer therapies, especially ones that are effective for treating solid tumors and address the drug resistance problem.

Artemisinin-based combination therapies (ACTs) have proven efficacious against multi-drug resistant parasites and are now employed by more than 60 countries following World Health Organization's recommendations. Coartem™ is an example of an ACT indicated for the treatment of acute uncomplicated plasmodium falciparum malaria, the most dangerous form of the disease. It is one of the most successful malaria treatments of its kind, being a highly effective and well-tolerated treatment. It provides cure rates of up to 97%, even in areas of multi-drug resistance.

Coartem has two active pharmaceutical ingredients; a derivative of artemisinin called artemether and lumefantrine (aka benflumetol) an antimalarial drug. This combination of ingredients is discussed in U.S. Pat. No. 5,677,331 issued Oct. 14, 1997. The composition can be formulated into solid dosage forms such as tablets and is useful for the treatment of drug-resistant malaria. The use of lumefantrine for constructing synergistic antimalarial compositions is also described in U.S. Pat. No. 5,637,594 issued Jun. 10, 1997.

Lumefantrine (IUPAC name: 2-(dibutylamino)-1-[(9E)-2,7-dichloro-9-(4-chlorobenzylidene)-9H-fluoren-4-yl]ethanol, CAS number: 82186-77-4) is an aminoalcohol which exists as a 1:1 racemic mixture of dextrorotatory and levorotatory enantiomers.

Several other compounds have been used as alternatives to lumefantrine in formulating ACTs for treating malaria. Examples of these compounds are discussed in the U.S. Pat. No. 5,637,594. These include halofantrine, amodiaquine, quinine, mefloquine, chloroquine, pamaquine, primaquine, tafenoquine, quinacrine, mepacrine and pyronaridine. Piperaquine is part of ACT therapy known as (Duo-Cotecxin™). Napthoquine has been clinically evaluated as component in an ACT.

A leading model of ACT anti-plasmodial activity hypothesizes that iron-mediated cleavage of the endoperoxide bridge within the artemisinin compound generates cytotoxic drug metabolites capable of damaging cellular macromolecules. In the parasite digestive food vacuole, neutral lipids are closely associated with heme and promote hemozoin formation. It is likely that artemisinin and its derivatives are activated by heme-iron within neutral lipid environment of the food vacuole. In mammalian cells the analogous digestive compartment to food vacuoles is the lysosome.

BRIEF SUMMARY OF THE INVENTION

Lumefantrine, currently used in treatment of malaria, has utility in the treatment of cancer either used alone and as part of combination therapy with another drug. Other compounds related to lumefantrine by structure and/or by their use in ACTs, have utility in the treatment of cancer either used alone and as part of combination therapy with another drug.

DETAILED DESCRIPTION OF THE INVENTION

Tumor recalcitrance or resistance to chemotherapy derives from, among other things, changes in metabolic pathways that allow them to survive chemotherapy.

One ubiquitous adaptive survival response is autophagy, a catabolic "self-eating" process that cells use to recover metabolic substrates for reuse from, e.g., misfolded proteins. It is often induced when nutrients become limiting, such as during stressful or starvation conditions. The most thoroughly characterized form of autophagy is macroautophagy. It involves sequestration of damaged organelles and unused intracellular proteins into double-membranes vesicles called autophagosomes (aka autophagic vacuoles). The lysosome plays an essential part in macroautophagy, fusing with autophagosomes to form autophagolysosome (aka autolysosome) wherein the contents are degraded.

It is becoming increasingly clear that the cytotoxic response, whether induced by traditional chemotherapeutics or targeted-therapies, is dictated by the endoplasmic reticulum (ER) stress created in the tumor. Endoplasmic stress is created by misfolded proteins, but also can be induced through disruptions in ER and cytosolic calcium homeostasis associated with the depletion of ER calcium stores and increases in intracellular calcium. Endoplasmic reticulum stress activates the protective unfolded protein response (UPR) in an attempt to match the protein-folding capacity of the ER with cellular demands and to survive the stress. The UPR coordinates the up-regulation of distinct proteins including ER chaperones and folding machinery, and components necessary for ER-associated degradation (ERAD) essential for decreasing ER stress by clearing terminally misfolded proteins from the ER. Persistent release of calcium from the ER leads to increased mitochondrial calcium uptake, causing a rise of mitochondrial matrix-free calcium, activation of caspases, and eventual cell death. ER stress also affects the morphology, integrity, and the sub-cellular location of vesicles including early endosomes, late endosomes, and lysosomes. Repetitive but futile folding attempts not only prolong ER stress but can also result in reactive oxygen species (ROS) generation, both of which may result in cell death.

Cancer chemotherapy-induced ER stress also induces a protective autophagy response in the tumor cells. Autophagy serves as quality control system to remove potentially toxic misfolded proteins and thereby promotes drug non-responsiveness or resistance in the tumor. Equally important though, it allows for tumor cells to reduce their metabolic needs and enter into a protected quiescent state (i.e. "safe harbor") well suited for resisting cytotoxic insults.

Effective treatment of cancer depends on overwhelming or circumventing the protective survival responses induced by ER stress in the tumor.

Cancer chemotherapeutics which induce endoplasmic reticulum stress are collectively referred to as "ER stressor drugs", or singularly as an "ER stressor drug". Research indicates that inhibition of autophagy enhances that the capacity of ER stressor drugs to kill tumor cells.

This application discloses that the anti-malarial drug lumefantrine has utility in the treatment of cancer, where it is thought to work by inhibiting autophagy. By blocking autophagy, lumefantrine, or its metabolite desbutyl-lumefantrine, prevents the tumor from entering a protected quiescent state. Lumefantrine, or its metabolite desbutyl-lumefantrine, may be used in cancer treatment either alone, but more preferentially as part of a combination therapy with an ER stressor drug.

Examples of suitable drug classes that function as ER stressor drugs include members of the artemisinin family, proteasome inhibitors, histone deacetylase inhibitors, Bcr-Abl inhibitors, tyrosine kinase inhibitors, HIV protease inhibitors, biguanides, and sarcolemmal Na(+)/H(+) exchanger (NHE)1 inhibitors. Specific examples of artemisinin family members that induce ER stress include artemisinin itself, and artesunate, artemesin, artemether, arteether (aka artemotil), artemisinin, artemisetene, arteanuine B, and dihydroartemisinin. Specific examples of proteasome inhibitors which induce ER stress include bortezomib, carfilzomib, and disuliram. Specific examples of histone deacetylase inhibitors which induce ER stress include suberoylanilide hydroxamic acid, valproic acid, belinostat, and vorinostat. Specific examples of Bcr-Abl inhibitors which induce ER stress include imatinib, dasatinib, nilotinib, ponatinib, bosutinib, INNO-406, AZD0530, and MK-0457. Specific examples of tyrosine kinase inhibitors which induce ER stress include sorafenib, erlotinib, gefitinib, lapatinib, and trastuzumab. Specific examples of HIV protease inhibitors which induce ER stress include ritonavir, saquinavir, amprenavir, lopinavir, nelfinavir, atazanavir, indinavir, fosamprenavir, darunavir, tipranavir, and the combination of saquinavir and ritonavir. Specific examples of biguanides which induce ER stress include metformin, phenformin, buformin, and proguanil. Specific examples of sarcolemmal Na(+)/H(+) exchanger (NHE)1 inhibitors which induce ER stress include amiloride, cariporide, 5-(N, N-hexamethylene)-amiloride (HMA), 5-(N-methyl-N-isobutyl) amiloride, and 5-(N-ethyl-N-isopropyl) amiloride (EIPA). Other drugs which induce ER stress include riluzole, temozolomide, gemcitabine, paclitaxel, protein-bound paclitaxel (Abraxane™), rituximab, niclosamide, fludarabine, mycophenolate, OZ439, and OZ277. These drugs are all ER stressor drugs by virtue of their ability to disrupt ER and cytosolic calcium homeostasis causing increases in intracellular calcium, to induce the unfolded protein response (UPR), to influence mitochondrial calcium uptake and calcium loads, to cause leakage of cathepsins from endosomes/lysosomes into the cytoplasm, and to activate caspases involved in mediating cell death responses.

This application additionally discloses that alternative drugs used in place of lumefantrine in formulating anti-malarial ACTs (i.e. "lumefantrine-alternative drugs") also have utility in the treatment of cancer, where they are also thought to work by inhibiting autophagy. Examples of suitable drug classes that act as lumefantrine-alternative drugs include quinolines and substituted acridines. Specific examples of lumefantrine-alternative drugs in ACTs which also have utility in treating cancer include amodiaquine, mefloquine, naphthoquine, pamaquine, primaquine, piperaquine, tafenoquine, quinacrine, mepacrine, halofantrine, pyronaridine, nitazoxanide, and atovaquone (alternative spelling: atavaquone). Lumefantrine-alternative drugs may be used in cancer treatment either alone, or as part of a combination therapy with an ER stressor drug. Lumefantrine-alternative drugs may be combined with the same drug classes, and the same specific examples, of ER stressor drugs as lumefantrine.

The exact formulation, route of administration and dosage for the pharmaceutical compositions of the present invention can be chosen by the individual physician in view of the patient's condition. (See e.g. Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage of each component may be a single one or a series of two or more given in the course of one or more days, as is needed by the patient. Note that for almost all of the specific compounds mentioned in the present disclosure, human dosages for treatment of at least some condition have been established. Thus, in most instances, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a case-by-case basis, some generalizations regarding the dosage can be made. The daily dosage regimen for an adult human patient may be, for example, an oral dose of between 0.1 mg and 6000 mg of each ingredient, preferably between 1 mg and 5000 mg, e.g. 25 to 5000 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions of the present invention or a pharmaceutically acceptable salt thereof calculated as the free base, the composition being administered 1 to 4 times per day. Alternatively the compositions of the invention may be administered by continuous intravenous infusion, preferably at a dose of each ingredient up to 400 mg per day. Thus, the total daily dosage by oral administration of each ingredient will typically be in the range 1 to 2500 mg and the total daily dosage by parenteral administration will typically be in the range 0.1 to 400 mg. Suitably the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen that maintains plasma levels above the MEC for 10-90% of the time, preferably between 30-90% and most preferably between 50-90%.

Lumefantrine or a salt thereof for use of the invention is most conveniently administered orally in unit dosage forms such as tablets or capsules, containing the active ingredient (calculated as the free form) in an amount from about 0.01 mg/kg/day to 100 mg/kg/day, preferably 0.01 mg/kg/day to 30 mg/kg/day body weight, more preferably 1.0 mg/kg/day to 30 mg/kg/day body weight. The same conditions also are applicable for dosing with desbutyl-lumefantrine or with the lumefantrine-alternative drugs.

When lumefantrine or desbutyl-lumefantrine are combined with other compounds in order to obtain an increased effect, or in order to allow for the use of a subnormal dose of the other compound, to minimize side effects, then subnormal doses of lumefantrine and/or the other compound may be used for the treatment. Calculation of patient specific doses is routine practice for those skilled in the art.

When lumefantrine-alternative drugs are combined with other compounds in order to obtain an increased effect, or in order to allow for the use of a subnormal dose of the other compound, to minimize side effects, then subnormal doses of lumefantrine and/or the other compound may be used for the treatment. Calculation of patient specific doses is routine practice for those skilled in the art.

In one embodiment, the present invention relates to the use of lumefantrine or a pharmaceutically acceptable salt thereof, together with an ER stressor drug in a synergistic effective dose for the preparation of a pharmaceutical composition as above, which is adapted for simultaneous administration of the active ingredients. In particular, such pharmaceutical compositions may contain the active ingredients within the same unit dosage form, e.g. in the same tablet or capsule. Such unit dosage forms may contain the active ingredients as a homogenous mixture or in separate compartments of the unit dosage form.

In another embodiment, the present invention relates to the use of desbutyl-lumefantrine or a pharmaceutically acceptable salt thereof, together with an ER stressor drug in a synergistic effective dose for the preparation of a pharmaceutical composition as above, which is adapted for simultaneous administration of the active ingredients. In particular, such pharmaceutical compositions may contain the active ingredients within the same unit dosage form, e.g. in the same tablet or capsule. Such unit dosage forms may contain the active ingredients as a homogenous mixture or in separate compartments of the unit dosage form.

In another embodiment, the present invention relates to the use of a lumefantrine-alternative drug or a pharmaceutically acceptable salt thereof, together with an ER stressor drug in a synergistic effective dose for the preparation of a pharmaceutical composition as above, which is adapted for simultaneous administration of the active ingredients. In particular, such pharmaceutical compositions may contain the active ingredients within the same unit dosage form, e.g. in the same tablet or capsule. Such unit dosage forms may contain the active ingredients as a homogenous mixture or in separate compartments of the unit dosage form.

In another embodiment, the present invention relates to the use of Coartem in treating cancer.

In another embodiment, the present invention relates to the use of lumefantrine or a pharmaceutically acceptable salt thereof, together with artemether in a synergistic effective dose for the treatment of cancer.

In another embodiment, the present invention relates to the use of lumefantrine or a pharmaceutically acceptable salt thereof, together with OZ439 in a synergistic effective dose for the treatment of cancer.

In another embodiment, the present invention relates to the use of lumefantrine or a pharmaceutically acceptable salt thereof, together with arterolane maleate in a synergistic effective dose for the treatment of cancer.

In another embodiment, the present invention relates to the use of amodiaquine or a pharmaceutically acceptable salt thereof, together with artesunate in a synergistic effective dose for the treatment of cancer.

In another embodiment, the present invention relates to the use of mefloquine or a pharmaceutically acceptable salt thereof, together with artesunate in a synergistic effective dose for the treatment of cancer.

In another embodiment, the present invention relates to the use of piperaquine or a pharmaceutically acceptable salt thereof, together with dihydroartemisinin in a synergistic effective dose for the treatment of cancer.

In another embodiment, the present invention relates to the use of piperaquine or a pharmaceutically acceptable salt thereof, together with OZ439 in a synergistic effective dose for the treatment of cancer.

In another embodiment, the present invention relates to the use of piperaquine or a pharmaceutically acceptable salt thereof, together with arterolane maleate in a synergistic effective dose for the treatment of cancer.

The pharmaceutical compositions and methods provided in the present invention are particularly deemed useful for the treatment of cancer including solid tumors such as skin, breast, brain, cervical carcinomas, testicular carcinomas, etc. More particularly, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple mycloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoina, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Thus, the term "cancer" includes but is not limited to any of the conditions identified above. Any of the above mentioned conditions are to be considered as single embodiments, and the compositions directed to the treatment of each condition may accordingly be claimed individually or be included in the claimed group when the term cancer is used.

Examples

The examples disclosed below are intended to illustrate but not limit the scope of the invention, which is defined by the claims.

A study conducted through the independent Cancer Therapy & Research Center, Institute for Drug Development at the University of Texas Health Science Center at San Antonio, Tex., evaluated lumefantrine as an autophagy inhibitor (i.e., "Lumefantrine Study"). The Lumefantrine Study addressed whether lumefantrine could enhance the ability of selected ER stressor drugs to inhibit the growth of two indicator cell lines: Ba/F3 cells expressing either the wild-type (p210) or mutant Bcr-Abl (T3150. The investigators had used this same test system in a previously published study (i.e., "Previous Study")(Reference: "Targeting autophagy augments the anticancer activity of the histone deacetylase inhibitor SAHA to overcome Bcr-Abl-mediated drug resistance. Carew J S, Nawrocki S T, Kahue C N, Zhang H, Yang C, Chung L, Houghton J A, Huang P, Giles F J, Cleveland J L. Blood. 2007 Jul. 1; 110(1):313-22. Epub 2007 Mar. 15. PMID: 17363733".

Tumor Cell Lines

Murine Ba/F3 cells that stably express wild-type BCR-ABL (p210) or the T315I mutated version of BCR-ABL, which confers resistance to imatinib and nilotinib were utilized for this study. Cells were propagated at 37° C. in a humidified atmosphere containing 5% carbon dioxide.

Cell Viability Assay

Cell viability was determined using the MTT assay. This colorimetric procedure measures conversion of the MTT reagent (a tetrazoleum salt) to formazan by mitochondria. Formazan production was quantified by spectrophotometric measurement at 570 nm and was proportional to viable cell number. Cells were cultured and treated with different concentrations of the agent(s) for 48 hours. Following treatment, 50 µl of MTT was added to each well and allowed to incubate for 1-3 hours at 37° C. Each well was aspirated and 200 µl of DMSO was added to each well to dissolve the formazan. Absorbance (OD) values were measured using a Bio-Tek microplate reader at a single wavelength of 570 nm.

Chloroquine (at a single final concentration of 25 µM) served as a control autophagy inhibitor. Lumefantrine was tested as potential autophagy inhibitor at final concentrations between one to forty micromolar. Chloroquine and lumefantrine were evaluated both alone and in combination with ER stressor drugs. The ER stressor drugs tested and their final concentrations were Gleevec™ (imatinib, Novartis, final 350 nM), Tasign™ (nilotinib, Novartis, final 35 nM) or Zolinza™ (suberoylanilide hydroxamic acid, Merck, final 1 µM). Both chloroquine and the ER stressor drugs were added to the assays at final concentrations designed to yield approximately a 50% reduction in cell viability. The lumefantrine dosing was designed to identify doses of lumefantrine that were equipotent to chloroquine.

Figure 1:
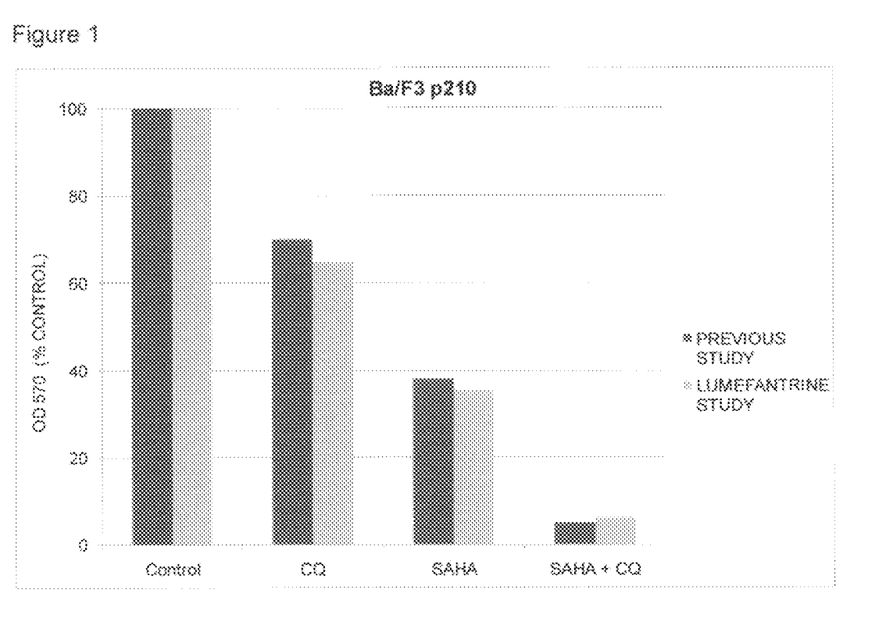
FIG. 1 shows the results from testing suberoylanilide hydroxamic acid (SAHA) together with chloroquine (CQ), a well-recognized inhibitor of autophagy, on the viability of Ba/F3 indicator cells expressing the wild-type (p210) Bcr-Abl (i.e. BA/F3 p210).

FIG. 1 shows that control autophagy inhibitor chloroquine (CQ) enhances the ability of suberoylanilide hydroxamic acid (SAHA) to block the proliferation of the Ba/F p210 cells. The values are means of triplicates. The "Previous Study" values in this figure were taken directly from FIG. 2E in "Targeting autophagy augments the anticancer activity of the histone deacetylase inhibitor SAHA to overcome Bcr-Abl-mediated drug resistance. Carew J S, Nawrocki S T, Kahue C N, Zhang H, Yang C, Chung L, Houghton J A, Huang P, Giles F J, Cleveland M. Blood. 2007 Jul. 1; 110(1):313-22. Epub 2007 Mar. 15. PMID: 17363733". The other values were generated in the "Lumefantrine Study" and are the same which are used in the construction of FIG. 2, and the error bars can be seen in that figure. Since the magnitude of the error bars were so small in the FIG. 2E from "Previous Study" values, rather than guess about their values, I decided to leave them off of this figure. The point of the figure is not affected by the absence of the error bars. The nearly identical mean OD 570 nm values obtained with the same samples evaluated in the two different studies suggest that the assay is highly reproducible and that blocking autophagy with chloroquine enhances the drug effects of SAHA.

FIGS. 2 through 7 shows the results obtained in testing lumefantrine (demarcated by the code name AUT001) with and without suberoylanilide hydroxamic acid, imatinib, and nolotinb on Ba/F3 indicator cells expressing either the wild-type (p210) Bcr-Abl or the mutant Bcr-Abl (T315I). Values are means+/−S.E.M. obtained with triplicates.

Figure 2:
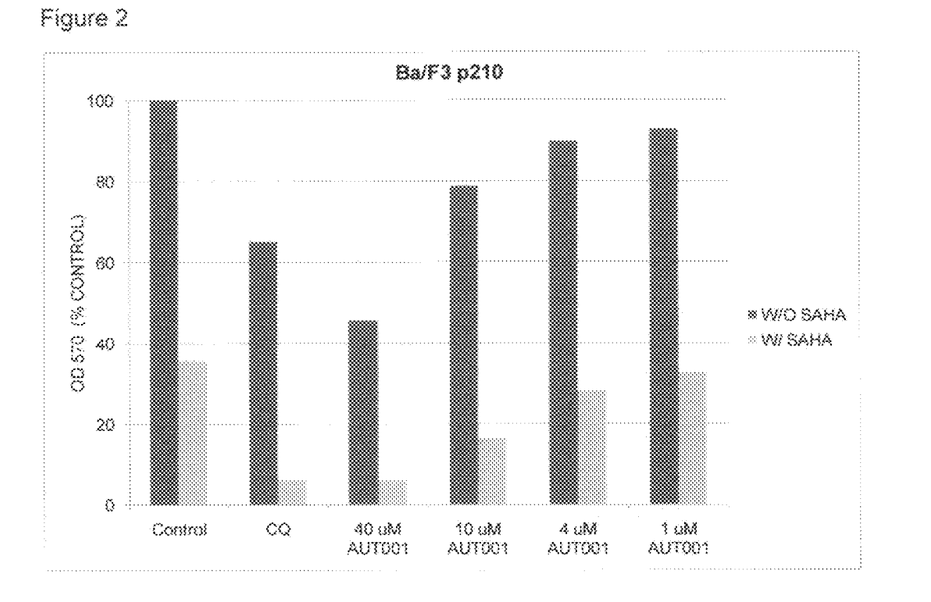
FIG. 2 and FIG. 3 show the results obtained in testing various doses of lumefantrine (denoted AUT001) in the presence (w/) and absence (w/o), respectively, of suberoylanilide hydroxamic acid (SAHA) on the viability of Ba/F3 indicator cells expressing either the wild-type (p210) Bcr-Abl (FIG. 2) or the mutant Bcr-Abl (T315I)(FIG. 3).
Figure 3:
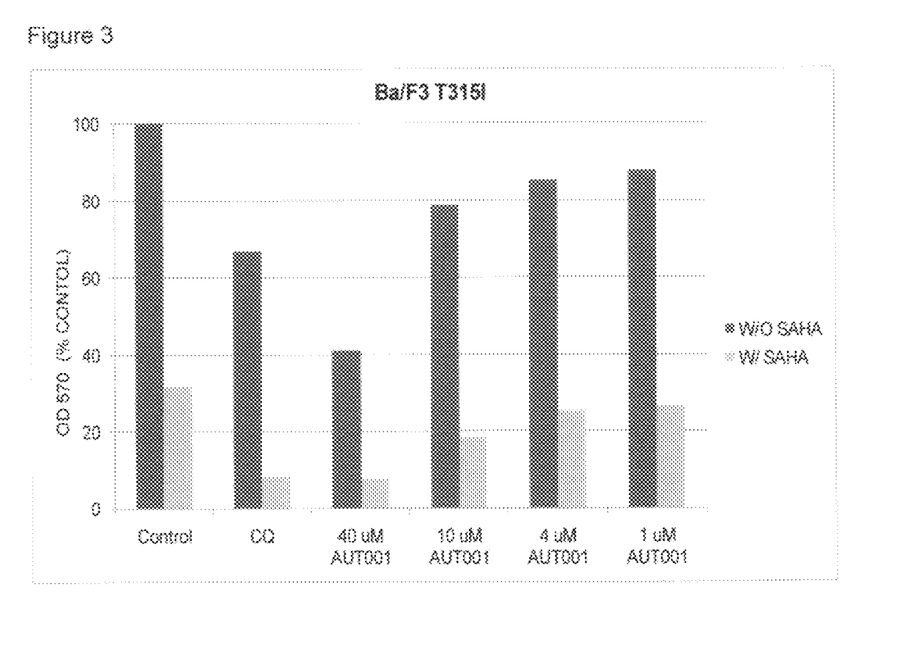

FIG. 2 and FIG. 3 show that lumefantrine (denoted AUT001) in the presence (w/) and absence (w/o), of suberoylanilide hydroxamic acid (SAHA) generates dose-dependent reductions in the cell viability. Similar effects are seen in the Ba/F3 indicator cells expressing either the wild-type (p210) Bcr-Abl or the mutant Bcr-Abl (T315I). Chloroquine (CQ) serves as the autophagy inhibitor control. Lumefantrine is equipotent with chloroquine for both cell-types. Values are means+/−S.E.M. obtained with triplicates.

Figure 4:
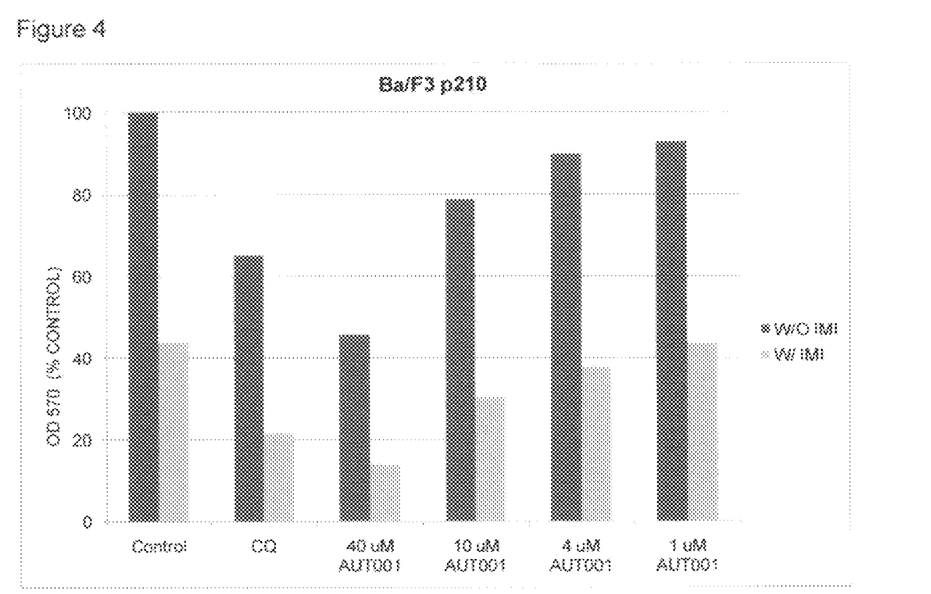
FIG. 4 and FIG. 5 show the results obtained in testing various doses of lumefantrine (denoted AUT001) in the presence (w/) and absence (w/o), respectively, of imatinib (IMI) on the viability of Ba/F3 indicator cells expressing either the wild-type (p210) Bcr-Abl (FIG. 4) or the mutant Bcr-Abl (T315I)(FIG. 5).
Figure 5:
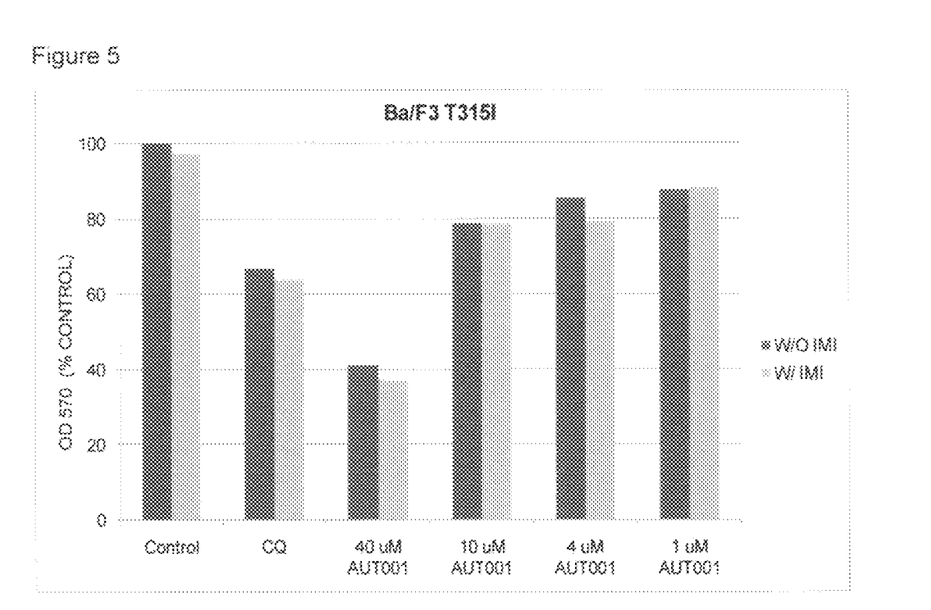

FIG. 4 and FIG. 5 show the results obtained in testing lumefantrine (denoted AUT001) in the presence (w/) and absence (w/o), respectively, of imatinib (IMI). Lumefantrine only augments the imatinib effects on the Ba/F3 indicator cells expressing the wild-type (p210) Bcr-Abl. In the Ba/F3 indicator cells expressing the mutant Bcr-Abl the only effects on viability are those generated by lumefantrine alone. The same patterns of reactivity for the two cell types were also obtained with chloroquine (CQ). Lumefantrine was equipotent with chloroquine for both cell-types. The values are means+/−S.E.M. obtained with triplicates.

Figure 6:
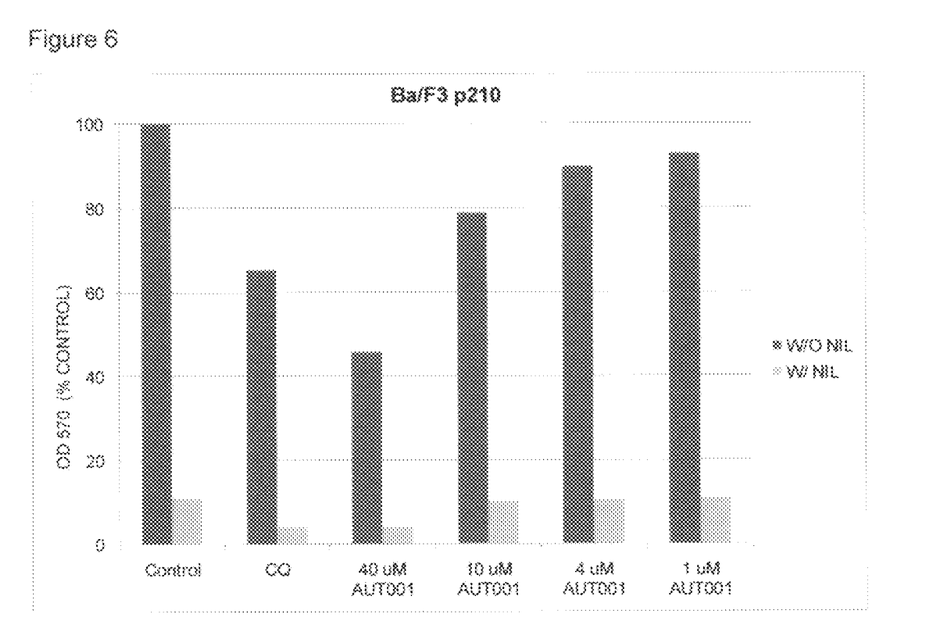
FIG. 6 and FIG. 7 show the results obtained in testing various doses of lumefantrine (denoted AUT001) in the presence (w/) and absence (w/o), respectively, of nolotinb (NIL) on the viability of Ba/F3 indicator cells expressing either the wild-type (p210) Bcr-Abl (FIG. 6) or the mutant Bcr-Abl (T315I)(FIG. 7).
Figure 7:
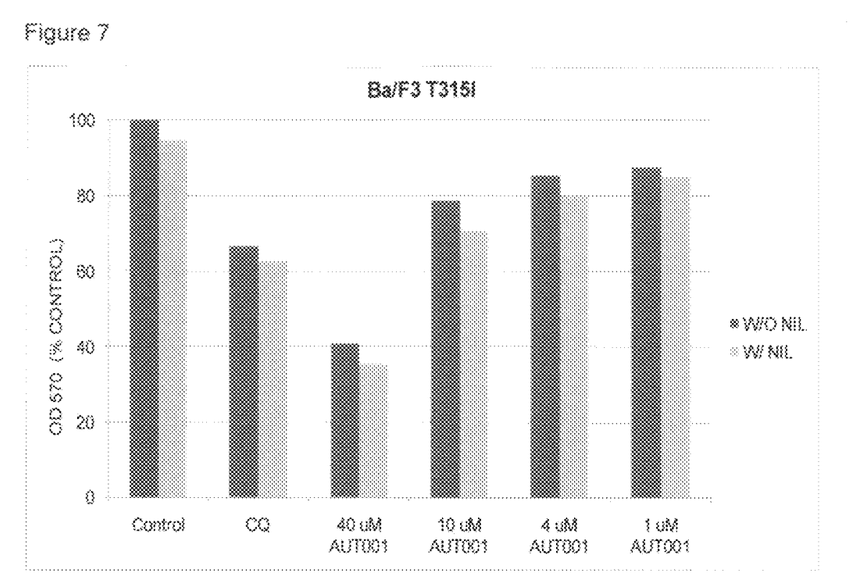

FIG. 6 and FIG. 7 show the results obtained in testing lumefantrine (denoted AUT001) in the presence (w/) and absence (w/o), respectively, of nolotinb (NIL). Lumefantrine only augments the nolotinb effects on the Ba/F3 indicator cells expressing the wild-type (p210) Bcr-Abl. In the Ba/F3 indicator cells expressing the mutant Bcr-Abl the only effects on viability are those generated by lumefantrine alone. The same patterns of reactivity for the two cell types were also obtained with chloroquine (CQ). Lumefantrine was equipotent with chloroquine for both cell-types. Values are means+/−S.E.M. obtained with triplicates.

In these experiments lumefantrine showed equal potency with chloroquine for each drug and cell-type, and further enhanced the ability of suberoylanilide hydroxamic acid, imatinib, and nolotinb to inhibit proliferation of Ba/F cells harboring the wild-type (p210) Bcr-Abl. In addition, lumefantrine enhanced the suberoylanilide hydroxamic acid drug response in both cells harboring the wild-type (p210) Bcr-Abl or the mutant Bcr-Abl (T315I).

The study results are consistent with the notion that lumefantrine is an autophagy inhibitor, and can enhance the capacity of ER stressor drugs to reduce the viability of cancer cells. The study results are consistent with the notion that drugs which are combined with artemisinins in antimalarial combination therapies (i.e. ACTs) act as autophagy inhibitors.

The invention claimed is:

1. A method of treating cancer in a patient in need thereof, comprising administration to said patient lumefantrine or desbutyl-lumefantrine in combination with an ER stressor drug selected from the group consisting of a histone deacetylase inhibitor and a Bcr-Abl inhibitor.

2. The method of claim 1, wherein lumefantrine or desbutyl-lumefantrine is administered to a patient in need thereof in a therapeutically effective dosage.

3. The method of claim 2, wherein lumefantrine or desbutyl-lumefantrine is administered to a patient in need thereof at a dosage between 1 and 30 mg/kg.

4. The method of claim 1, wherein the ER stressor drug is a histone deacetylase inhibitor selected from the group consisting of suberoylanilide hydroxamic acid, valproic acid, belinostat, and vorinostat.

5. The method of claim 1, wherein the ER stressor drug is a Bcr-Abl inhibitor selected from the group consisting of imatinib, dasatinib, nilotinib, ponatinib, bosutinib, INNO-406, AZD0530, and MK-0457.

6. A pharmaceutical composition comprising lumefantrine and an ER stressor drug selected from the group consisting of a histone deacetylase inhibitor and a Bcr-Abl inhibitor.

7. A pharmaceutical composition comprising desbutyl-lumefantrine and an ER stressor drug selected from the group consisting of a histone deacetylase inhibitior and a Bcr-Abl inhibitor.

* * * * *